United States Patent
Wang

(10) Patent No.: US 6,985,227 B2
(45) Date of Patent: Jan. 10, 2006

(54) BIREFRINGENCE MEASUREMENT AT DEEP-ULTRAVIOLET WAVELENGTHS

(75) Inventor: Baoliang Wang, Beaverton, OR (US)

(73) Assignee: Hinds Instruments, Inc., Hillsboro, OR (US)

( * ) Notice: Subject to any disclaimer, the term of this patent is extended or adjusted under 35 U.S.C. 154(b) by 0 days.

(21) Appl. No.: 10/730,583

(22) Filed: Dec. 8, 2003

(65) Prior Publication Data

US 2004/0114142 A1   Jun. 17, 2004

Related U.S. Application Data

(63) Continuation of application No. PCT/US02/19343, filed on Jun. 17, 2002.

(60) Provisional application No. 60/299,316, filed on Jun. 18, 2001, provisional application No. 60/336,219, filed on Oct. 31, 2001, provisional application No. 60/340,760, filed on Dec. 11, 2001.

(51) Int. Cl.
*G01J 4/00* (2006.01)

(52) U.S. Cl. ...................... 356/364; 356/365
(58) Field of Classification Search ........ 356/364–370; 250/225, 226

See application file for complete search history.

(56) References Cited

U.S. PATENT DOCUMENTS

| | | |
|---|---|---|
| 3,902,805 A | 9/1975 | Redner |
| 4,400,062 A | 8/1983 | Mori |
| 4,480,916 A | 11/1984 | Bareket |
| 4,668,086 A | 5/1987 | Redner |
| 4,725,145 A | 2/1988 | Azzam |
| 4,801,798 A | 1/1989 | Lange |
| 4,850,710 A | 7/1989 | Mochida |
| 4,904,931 A | 2/1990 | Miller |
| 4,973,163 A | 11/1990 | Sakai |
| 5,072,111 A | 12/1991 | Gilino |
| 5,268,741 A | 12/1993 | Chou |
| 5,311,284 A | 5/1994 | Nishino |
| 5,319,194 A | 6/1994 | Yoshizumi |
| 5,457,536 A | 10/1995 | Kornfield |
| 5,521,705 A | 5/1996 | Oldenbourg |
| 5,532,823 A | 7/1996 | Fukui |
| 5,536,936 A | 7/1996 | Drevillon |
| 5,652,673 A | 7/1997 | Oakberg |

(Continued)

OTHER PUBLICATIONS

Modine et al., "High frequency polarization modulation method for measuring birefringence", Applied Optics, vol. 14, No. 3, pp. 757-760, Mar. 1975.

(Continued)

*Primary Examiner*—Michael P. Stafira
(74) *Attorney, Agent, or Firm*—ipsolon llp

(57) ABSTRACT

Provided are systems and methods for precisely measuring birefringence properties of optical elements, especially those elements that are used in deep ultraviolet (DUV) wavelengths. The system includes two photoelastic modulators (PEM) (126, 128) located on opposite sides of the sample (136). Each PEM is operable for modulating the polarity of a light beam that passes though the sample. The system also includes a polarizer (124) associated with one PEM, an analyzer (130) associated with the other PEM, and a detector (132) for measuring the intensity of the light after it passes through the PEMs, polarizer, and analyzer. Described are techniques for determining birefringence properties across a wide range. For example, a dual-wavelength source light embodiment is provided for measuring relatively high levels of birefringence. Also provided is a technique for selecting the most accurate and efficient one of a number of approaches to determining birefringence properties depending upon the estimated value of the birefringence to be detected for a given sample optical element.

22 Claims, 4 Drawing Sheets

U.S. PATENT DOCUMENTS

| | | |
|---|---|---|
| 5,744,721 A | 4/1998 | Varnum |
| 5,825,492 A | 10/1998 | Mason |
| 5,864,403 A | 1/1999 | Ajji |
| 5,956,146 A | 9/1999 | Nakagawa |
| 5,956,147 A | 9/1999 | Jellison, Jr. |
| 6,023,332 A | 2/2000 | Bergstrom |
| 6,055,053 A | 4/2000 | Lesniak |
| 6,078,042 A | 6/2000 | Fellows |
| 6,268,914 B1 | 7/2001 | Wang et al. |
| 6,456,361 B1 | 9/2002 | Suzuki et al. |
| 6,473,179 B1 | 10/2002 | Wang et al. |
| 6,473,181 B1 | 10/2002 | Oakberg |
| 6,697,157 B2 | 2/2004 | Wang et al. |
| 6,738,137 B2 | 5/2004 | Oakberg |
| 2002/0192579 A1 | 12/2002 | Kamono |

OTHER PUBLICATIONS

E Mochida, "Measurement of Birefringence by Phase Modulating Method and Application Thereof", Opt Tech Contact vol. 27, No. 3 (1989), pp. 12.

Ohmi, W. et al, "High-sensitivity two-dimensional therma- and mechanical-stress-induced birefringence measurements in a Nd:YAG rod" APP'd Optics, Sep. 1994.

Kemp, J.; Piezo-Optical Birefringence Modulators: New Use for a Long-Known Effect; Journal of the Optical Society; vol. 59, No. 8, pp 950-954 (Aug. 1969).

Frattini & Fuller; Phase-Modulated Flow Birefringence; Journal of Rheology; vol. 28; Feb. 1984.

Ware, P. Progress Report: 157-nm Lithography Prepares to Graduate, SPIE's oe magazine, Feb. 2003, pp 14-16.

Mattison D. W., Diode-Laser Sensors for Pulse Detonation Engine Applications, AIAA, Jan. 2002, 5 pp. 1-5.

BIREFRINGENCE MEASUREMENT AT DEEP-ULTRAVIOLET WAVELENGTHS

TECHNICAL FIELD

This application relates to precise measurement of birefringence properties of optical elements, including optical elements that are components of systems that use deep ultraviolet (DUV) wavelengths.

BACKGROUND

Many important optical materials exhibit birefringence. Birefringence means that different linear polarizations of light travel at different speeds through the material. These different polarizations are most often considered as two components of the polarized light, one being orthogonal to the other.

Birefringence is an intrinsic property of many optical materials, and may also be induced by external forces. Retardation or retardance represents the integrated effect of birefringence acting along the path of a light beam traversing the sample. If the incident light beam is linearly polarized, two orthogonal components of the polarized light will exit the sample with a phase difference, called the retardance. The fundamental unit of retardance is length, such as nanometers (nm). It is frequently convenient, however, to express retardance in units of phase angle (waves, radians, or degrees), which is proportional to the retardance (nm) divided by the wavelength of the light (nm). An "average" birefringence for a sample is sometimes computed by dividing the measured retardation magnitude by the thickness of the sample.

Oftentimes, the term "birefringence" is interchangeably used with and carries the same meaning as the term "retardance." Thus, unless stated otherwise, those terms are also interchangeably used below.

The two orthogonal polarization components described above are parallel to two orthogonal axes, which are determined by the sample and are respectively called the "fast axis" and the "slow axis." The fast axis is the axis of the material that aligns with the faster moving component of the polarized light through the sample. Therefore, a complete description of the retardance of a sample along a given optical path requires specifying both the magnitude of the retardance and its relative angular orientation of the fast (or slow) axis of the sample.

The need for precise measurement of birefringence properties has become increasingly important in a number of technical applications. For instance, it is important to specify linear birefringence (hence, the attendant induced retardance) in optical elements that are used in high-precision instruments employed in semiconductor and other industries.

Moreover, the optical lithography industry is currently transitioning to the use of very short exposure wavelengths for the purpose of further reducing line weights (conductors, etc.) in integrated circuits, thereby to enhance performance of those circuits. In this regard, the next generation of optical lithography tools will use laser light having a wavelength of about 157 nanometers, which wavelength is often referred to as deep ultraviolet or DUV.

It is important to precisely determine the retardance properties of optical elements or components that are used in systems, such as lithography tools, that employ DUV. Such a component may be, for example, a calcium fluoride ($CaF_2$) lens of a scanner or stepper. Since the retardance of such a component is a characteristic of both the component material as well as the wavelength of light penetrating the material, a system for measuring retardance properties must operate with a DUV light source and associated components for detecting and processing the associated light signals.

The magnitude of the measured retardance of an optical element is a function of the thickness of the element, the thickness being measured in the direction that the light propagates through the sample. For example, a $CaF_2$ optical element will have an intrinsic birefringence of about 12 nm for every centimeter (cm) of thickness. Consequently, for example, a 10 cm-thick $CaF_2$ element will have a relatively high birefringence level of about 120 nanometers, which is about three-quarters of a 157 nm DUV wavelength.

SUMMARY OF THE INVENTION

The present invention is directed to systems and methods for precisely measuring birefringence properties of optical elements, especially those elements that are used in DUV applications.

In one preferred embodiment, the system includes two photoelastic modulators (PEM) located on opposite sides of the sample. Each PEM is operable for modulating the polarity of a light beam that passes though the sample. The system also includes a polarizer associated with one PEM, an analyzer associated with the other PEM, and a detector for measuring the intensity of the light after it passes through the PEMs, the polarizer, and the analyzer.

As one aspect of the invention, embodiments and methods are described for determining birefringence properties across a wide range. For example, an embodiment comprising a dual-wavelength light source is provided for measuring relatively high levels of birefringence.

Also provided is a technique for selecting the most accurate and efficient one of a number of approaches to determining birefringence properties of DUV optical elements, the selection depending upon the estimated level of the birefringence to be detected for a given optical sample.

The birefringence properties (retardance magnitude and/or angular orientation) are precisely calculated. The system permits multiple measurements to be taken across the area of a sample to detect and graphically display variations in the retardance across the sample area.

Other advantages and features of the present invention will become clear upon study of the following portion of this specification and drawings.

BEST MODES FOR CARRYING OUT THE INVENTION

One system for measuring birefringence is described in published International Patent Application No. WO99/42796, as well as in U.S. patent application Ser. No. 09/308,747, hereby incorporated by reference. That system employs a photoelastic modulator (PEM) for modulating polarized light that is then directed through a sample. The beam propagating from the sample is separated into two parts. These separate beam parts are then analyzed at different polarization directions, detected, and processed as distinct channels. The detection mechanisms associated with each channel detect the light intensity corresponding to each of the two parts of the beam. This information is employed in an algorithm for calculating a precise, unambiguous measure of the retardance induced by the sample as well as the angular orientation of birefringence relative to the fast axis of the sample. Considerations such as the nature of the light source required for retardance measurement at deep ultraviolet wavelengths (DUV) introduce the need for a somewhat different approach to birefringence measurement in the DUV environment.

One preferred embodiment of the present invention uses a dual PEM setup to measure low-level linear birefringence in optical elements. This embodiment determines birefringence properties (both magnitude and angular orientation) that are the most important ones for $CaF_2$ and fused silica suppliers to the semiconductor industry. This embodiment has specifically designed signal processing, a data collection scheme, and an algorithm for measuring low-level linear birefringence at very high sensitivity.

Figure 1:
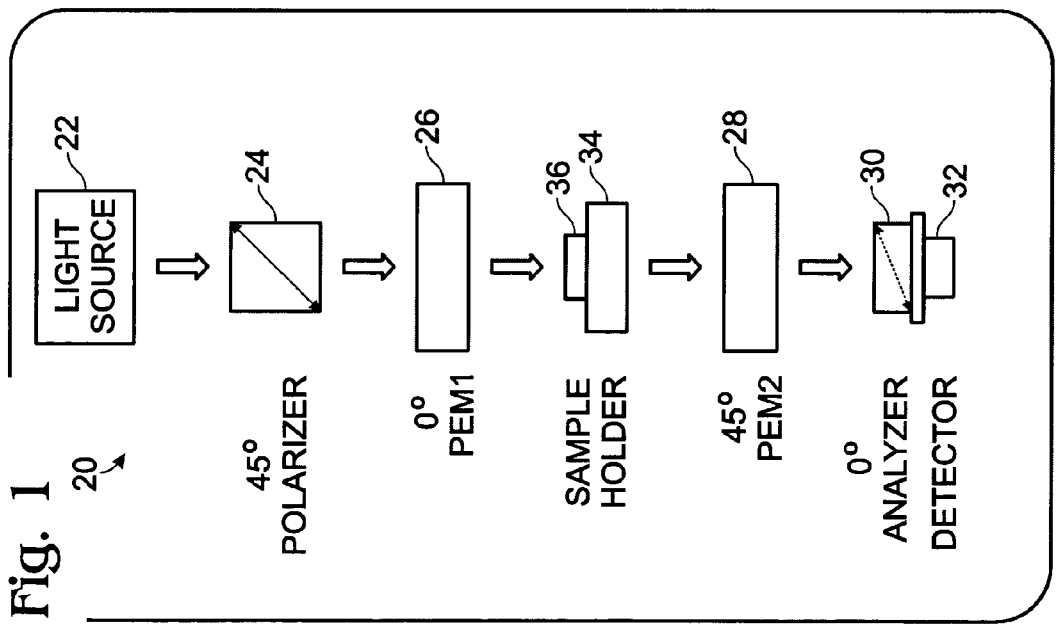
FIG. 1 is a diagram of one preferred embodiment of the present invention showing a preferred arrangement of the optical components of a birefringence measurement system.

As shown in FIG. 1, the dual-PEM setup 20 of this embodiment contains three modules. The top module comprises a light source 22, a polarizer 24 oriented at 45 degrees, and a PEM 26 oriented at 0 degrees.

The bottom module includes a second PEM 28 that is set to a modulation frequency that is different from the modulation frequency of the first PEM 20. The second PEM 28 is oriented at 45 degrees. The bottom module also includes an analyzer 30 at 0 degrees and a detector 32.

The middle module is a sample holder 34 that can be mounted on a computer-controlled X-Y stage to allow the scan of an optical element or sample 36.

This embodiment (FIGS. 1 and 2) employs as a light source 22 a polarized He—Ne laser at 632.8 nm. And, while the wavelength of this source is not DUV, the following is useful for explaining the general operation and analysis underlying the other dual-PEM embodiments explained below in connection with the DUV light sources that they employ.

With continued reference to FIG. 1, the polarizer 24 and analyzer 30 are each a Glan-Thompson-type polarizer. A Si-photodiode detector 32 is used in this embodiment. Both PEMs 26, 28 are bar-shaped, fused silica models having two transducers. The transducers are attached to the fused silica optical element with soft bonding material. To minimize birefringence induced in the optical element, only the transducers are mounted to the PEM housing. The two PEMs 26, 28 have nominal resonant frequencies of 50 and 55 KHz, respectively.

Figure 2:
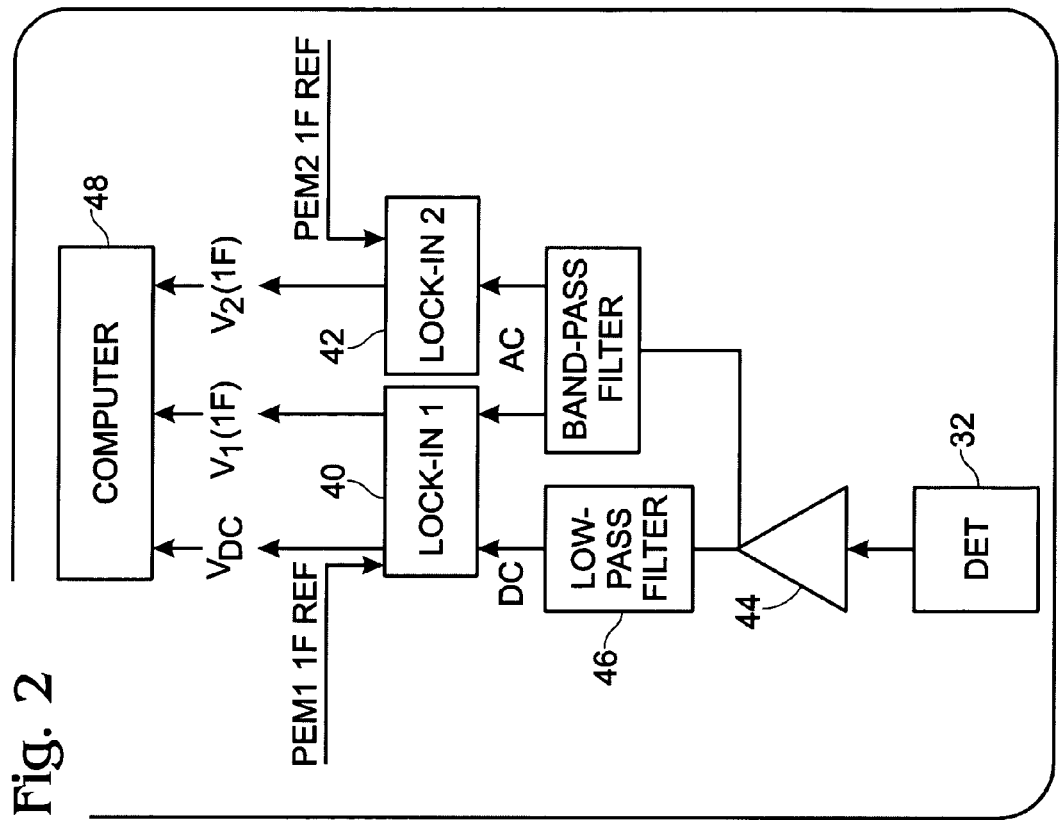
FIG. 2 is a block diagram of the processing components of the system depicted in FIG. 1.

With reference to FIG. 2, the electronic signals generated at the detector 32 contain both "AC" and "DC" signals and are processed differently. The AC signals are applied to two lock-in amplifiers 40, 42. Each lock-in amplifier, referenced at a PEM's fundamental modulation frequency (1F), demodulates the 1F signal provided by the detector 32. In a preferred embodiment, the lock-in amplifier is an EG&G Model 7265.

The DC signal is recorded after the detector 32 signal passes through an analog-to-digital converter 44 and a low-pass electronic filter 46. The DC signal represents the average light intensity reaching the detector 32. As discussed next, the DC and AC signals need to be recorded at different PEM retardation settings.

The theoretical analysis underlying the measurement of the birefringence properties of the sample 36 in this embodiment is based on a Mueller matrix analysis, and is discussed next for this dual PEM-single detector embodiment of FIGS. 1 and 2.

For clarity, the Mueller matrices for three of the optical components in FIG. 1 are shown below. The sample 36 in the optical arrangement, with a magnitude of $\delta$ and an angle of the fast axis at $\rho$, has the following form:

$$\begin{bmatrix} 1 & 0 & 0 & 0 \\ 0 & \cos(4\rho)\sin^2\left(\frac{\delta}{2}\right)+\cos^2\left(\frac{\delta}{2}\right) & \sin(4\rho)\sin^2\left(\frac{\delta}{2}\right) & -\sin(2\rho)\sin\delta \\ 0 & \sin(4\rho)\sin^2\left(\frac{\delta}{2}\right) & -\left(\cos(4\rho)\sin^2\left(\frac{\delta}{2}\right)\right)+\cos^2\left(\frac{\delta}{2}\right) & \cos(2\rho)\sin\delta \\ 0 & \sin(2\rho)\sin\delta & -\cos(2\rho)\sin\delta & \cos\delta \end{bmatrix}$$

The Mueller matrices of the two PEMs, with the retardation axes oriented at $\rho=0°$ and $45°$ are, respectively:

$$\begin{pmatrix} 1 & 0 & 0 & 0 \\ 0 & 1 & 0 & 0 \\ 0 & 0 & \cos(\delta 1) & \sin(\delta 1) \\ 0 & 0 & -\sin(\delta 1) & \cos(\delta 1) \end{pmatrix} \begin{pmatrix} 1 & 0 & 0 & 0 \\ 0 & \cos(\delta 2) & 0 & -\sin(\delta 2) \\ 0 & 0 & 1 & 0 \\ 0 & \sin(\delta 2) & 0 & \cos(\delta 2) \end{pmatrix}$$

where $\delta 1$ and $\delta 2$ are the time varying phase retardation of the first PEM 26 and second PEM 28 ($\delta 1 = \delta 1_o \sin \omega_1 t$ and $\delta 2 = \delta 2_o \sin \omega_2 t$; where $\omega_1$ and $\omega_2$ are the PEMs' modulating frequencies; $\delta 1_o$ and $\delta 2_o$ are the retardation amplitudes of the two PEMs).

Using the Mueller matrices of the optical components in the set-up shown in FIG. 1, the light intensity reaching the detector 32 is obtained as follows:

$$\frac{KI_0}{2}\left\{1+\cos(\delta 1)\cos(\delta 2)\sin(4\rho)\sin^2\left(\frac{\delta}{2}\right)+\sin(\delta 1)\sin(\delta 2)\cos\delta + \cos(\delta 1)\sin(\delta 2)\cos(2\rho)\sin\delta + \sin(\delta 1)\cos(\delta 2)\sin(2\rho)\sin\delta\right\} \quad \text{eqn. (1)}$$

where $I_0$ is the light intensity after the polarizer 24 and K is a constant that represents the transmission efficiency of the optical system after the polarizer.

The functions of sin δ1 and cos δ1 in equation 1 can be expanded with the Bessel functions of the first kind:

$$\sin\delta 1 = \sin(\delta 1_0 \sin(\omega_1 t)) = \sum_{2k+1} 2J_{2k+1}(\delta 1_0)\sin((2k+1)\omega_1 t) \quad \text{eqn. (2)}$$

where k is either "0" or a positive integer, and $J_{2k+1}$ is the $(2k+1)^{th}$ order of the Bessel function; and $$\cos\delta 1 = \cos(\delta 1_0 \sin(\omega_1 t)) = J_0(\delta 1_0) + \sum_{2k} 2J_{2k}(\delta 1_0)\cos((2k)\omega_1 t) \quad \text{eqn. (3)}$$

where $J_0$ is the $0^{th}$ order of the Bessel function, and $J_{2k}$ is the $(2k)^{th}$ order of the Bessel function.

Similar expansions can be made for sin δ2 and cos δ2.

Substituting the expansions of sin δ1, cos δ1, sin δ2 and cos δ2 into equation (1) and taking only up to the second order of the Bessel functions, we obtain the following terms:

$1 + [J_0(\delta 1_0) + 2J_2(\delta 1_0)\cos(2\omega_1 t)] \cdot [J_0(\delta 2_0) + 2J_2(\delta 2_0)\cos(2\omega_2 t)]$ term (1)

$\sin(4\rho)\sin^2\left(\frac{\delta}{2}\right)$ $2J_1(\delta 1_0)\sin(\omega_1 t) \cdot 2J_1(\delta 2_0)\sin(\omega_2 t) \cdot \cos\delta$ term (2)

$[J_0(\delta 1_0)+2J_2(\delta 1_0)\cos(2\omega_1 t)] \cdot [2J_1(\delta 2_0)\sin(\omega_2 t)] \cos(2\rho)\sin\delta = J_0(\delta 1_0) \cdot 2J_1(\delta 2_0)\sin(\omega_2 t)\cos(2\rho)\sin\delta + 2J_2(\delta 1_0)\cos(2\omega_1 t) \cdot 2J_1(\delta 2_0)\sin(\omega_2 t)\cos(2\rho)\sin\delta$ term (3)

$[J_0(\delta 2_0)+2J_2(\delta 2_0)\cos(2\omega_2 t)] \cdot [2J_1(\delta 1_0)\sin(\omega_1 t)] \sin(2\rho)\sin\delta = J_0(\delta 2_0) \cdot [2J_1(\delta 1_0)\sin(\omega_1 t)] \sin(2\rho)\sin\delta + 2J_2(\delta 2_0)\cos(2\omega_2 t) \cdot [2J_1(\delta 1_0)\sin(\omega_1 t)] \sin(2\rho)\sin\delta$ term (4)

The first parts of terms (3) and (4) can be used for determining linear retardance at low levels (below π/2 or a quarter-wave). Term (2) is useful for determining linear retardance at higher levels (up to π or a half-wave). Term (1) contains DC terms that relate to the average light intensity.

The 1F AC signals on the detector 32 can be determined using the lock-in amplifiers 40, 42 referenced at the PEMs' first harmonic (1F) frequencies. The lock-in amplifier will effectively exclude the contributions from all other harmonics. The IF signals measured by the lock-in amplifiers 40, 42 for the two PEMs 26, 28 are:

$$\sqrt{2} \cdot V_{1,1F} = \frac{KI_0}{2} J_0(\delta 1_0) \cdot 2J_1(\delta 2_0)\cos(2\rho)\sin\delta \quad \text{eqn. (4)}$$

$$\sqrt{2} \cdot V_{2,1F} = \frac{KI_0}{2} J_0(\delta 2_0) \cdot 2J_1(\delta 2_{01})\sin(2\rho)\sin\delta$$

where $\sqrt{2}$ results from the fact that the output of a lock-in amplifier measures the root-mean-square, not the signal amplitude. It is seen from eqn (4) that the maximum values of $J_0(\delta 1_0)2J_1(\delta 2_0)$ and $J_0(\delta 2_0)2J_1(\delta 1_0)$ will lead to optimal results for the output of the lock-in amplifiers. When the AC signals are collected, the retardation amplitudes of both PEMs are set to be 1.43 radians to optimize the AC signals.

The DC signal can be derived from term (1) to be:

$$V_{DC} = \frac{KI_0}{2}\left\{1 + J_0(\delta 1_0) \cdot J_0(\delta 2_0) \cdot \sin(4\rho)\sin^2\left(\frac{\delta}{2}\right)\right\} \quad \text{eqn. (5)}$$

where any term that varies as a function of the PEMs' modulation frequencies is omitted because they have no net contribution to the DC signal. The low-pass electronic filter 46 is used to eliminate such oscillations.

Within small angle approximation (sin X=X and $\sin^2 X$=0 when X is small), $V_{DC}$ is independent of the sample's retardation and thus represents the average light intensity reaching the detector. However, when a sample with retardation above 30 nm is measured, the $V_{DC}$ as shown in equation (5) will generally be affected by the magnitude and angle of the retardance. Thus, the measured DC signal will not be a true representation of the average light intensity. In this case, the most straightforward method is to set both $J_0(\delta 1_0)$ and $J_0(\delta 2_0)$ equal to "0". The DC signal then becomes:

$$V_{DC} = \frac{KI_0}{2} \quad \text{eqn. (6)}$$

In this embodiment, the PEMs' retardation amplitude was selected as $\delta 1_0 = \delta 2_0 = 2.405$ radians (0.3828 waves) for recording the DC signal. At such PEM settings, $J_0(\delta 1_0) = J_0(\delta 2_0) = 0$. Therefore, the DC signal, independent of ρ or δ, truly indicates the average light intensity reaching the detector.

As seen, this method requires recording AC and DC signals at different PEM settings and thus has a slower measurement speed (about 2 seconds per data point). This method affords high accuracy measurement of linear retardance above 30 nm. When speed is critical, an alternative method can be used. If the DC signal is collected at $\delta 1_0 = \delta 2_0 = 01.43$ radians, where the AC signals are recorded, the measured retardance of a sample, using the ratio of AC to DC, will depend on the sample's angular orientation. However, the DC term is well defined in equation (5). It is, therefore, possible to reduce the angular dependence of retardance by iteration of calculation for both retardation magnitude and angle.

In order to eliminate the effect of light intensity variations due to light source fluctuations and the absorption, reflection and scattering from the sample and other optical components, the ratio of the 1F AC signal to the DC signal are used. The ratios of AC signals to the DC signal for both PEMs are represented in equation (7):

$$\frac{\sqrt{2} \cdot V_{1,1F}}{V_{DC}} = J_0(\delta 1_0) \cdot 2J_1(\delta 2_0)\sin\delta\cos(2\rho) \quad \text{eqn. (7)}$$

$$\frac{\sqrt{2} \cdot V_{2,1F}}{V_{DC}} = J_0(\delta 2_0) \cdot 2J_1(\delta 1_0)\sin\delta\sin(2\rho)$$

Defining $R_1$ and $R_2$ as corrected ratios for both PEMs yields:

$$\frac{\sqrt{2} \cdot V_{1,1F}}{J_0(\delta 1_0) \cdot 2J_1(\delta 2_0) \cdot V_{DC}} = R_1 = \sin\delta\cos(2\rho) \quad \text{eqn. (8)}$$

-continued $$\frac{\sqrt{2}\cdot V_{2,1F}}{J_0(\delta 2_0)\cdot 2J_1(\delta 1_0)\cdot V_{DC}} = R_2 = \sin\delta\sin(2\rho)$$

Finally, the magnitude and angular orientation of the birefringence are expressed as:

$$\rho = \frac{1}{2}\tan^{-1}\left[\frac{R_2}{R_1}\right] \text{ or } \rho = \frac{1}{2}ctg^{-1}\left[\frac{R_1}{R_2}\right] \quad \text{eqn. (9)}$$

$$\delta = \arcsin\left(\sqrt{(R_1)^2 + (R_1)^2}\right)$$

where δ, represented in radians, is a scalar. When measured at a specific wavelength (i.e., 632.8 nm), it can be converted to retardation in nanometers: dnm= drad(632.8/(2π)).

It should be emphasized that equations (9) are specifically developed for small linear birefringence due to the use of arcsine function in determining linear birefringence. Therefore, this method described here has a theoretical upper limit of π/2 or 158.2 nm when using 632.8 nm laser as the light source.

The signals at both PEMs' modulation frequencies depend on the orientation of the fast axis of the sample (see equation (6)), and the final retardation magnitudes are independent of the fast axis angles (see equation (9)). To achieve this angular independence of retardation magnitude, it is important to accurately orient all optical components in the system (as well as those of the embodiments described below).

In this embodiment, the first PEM's optical axis is used as the reference angle ("0°"). All other optical components in the system are accurately aligned directly or indirectly with this reference angle. With the first PEM 26 being fixed, the following procedures ensure the accurate alignment of all other optical components in the system:

1. With the second PEM 28 (50 KHz) being turned off and the first PEM 26 (55 KHz) operating at quarter-wave peak retardation, the polarizer 24 and analyzer 30 are approximately oriented at +45 degrees and −45 degrees, respectively.
2. Rotate the polarizer 24 in fine increments while monitoring the 2F (110 kHz) signal from lock-in amplifier 40. When the 2F signal reaches its minimum (usually <0.05 mV with a lock-in sensitivity of 1 mV), read precisely the angle on the rotation stage of the polarizer 24.
3. Rotate the polarizer 24 by precisely 45°, which is the correct position for the polarizer.
4. Once the orientation of the polarizer 24 is correctly established, rotate the analyzer 30 in front of the detector 32 until the 2F (110 kHz) signal from lock-in amplifier 40 reaches its minimum.
5. With the first PEM 26 (55 KHz) being turned off and the second PEM 28 (50 KHz) operating at quarter-wave peak retardation, rotate the second PEM until the second 42 lock-in amplifier's 2F (100 kHz) signal reaches its minimum.

When the optical components are misaligned, retardation magnitude shows specific patterns of angular dependence.

The birefringence measurement of the present embodiment is specifically designed for accurately measuring low-level linear birefringence. In order to accurately measure such low levels of retardation, it is critical to correct for the existing residual linear birefringence of the instrument itself (instrument offset) even when high quality optical components are used.

The instrument offset is primarily due to the small residual linear birefringence in the PEMs (on the order of 0.1 nm). To correct the system offset, an average of several measurements without any sample is first obtained. The instrument offsets are corrected in the software when a sample is measured. Notice that such corrections should only be done when the ratios are calculated using equations (8), not on the final results of δ and ρ, eqn. (9). The instrument offsets should be constants (within the instrumental noise level) unless there is a change in either the alignment of optical components or laboratory conditions such as temperature. It is prudent to check the instrument offsets with some regularity.

This offset correction works within the limit of small retardance when the Mueller matrices of retardance commute. In practice, this is the only case where an offset correction is needed. Since the residual retardation in the PEMs is so small (on the order of 0.1 nm), offset correction will not be necessary when measuring retardation higher than 50 nm.

The foregoing embodiment was specifically designed for measuring low-level retardance (up to a quarter-wave of the light source's wavelength, i.e. 158 nm for a 633 nm He—Ne laser; 39 nm for the 157 nm light).

Figure 4:
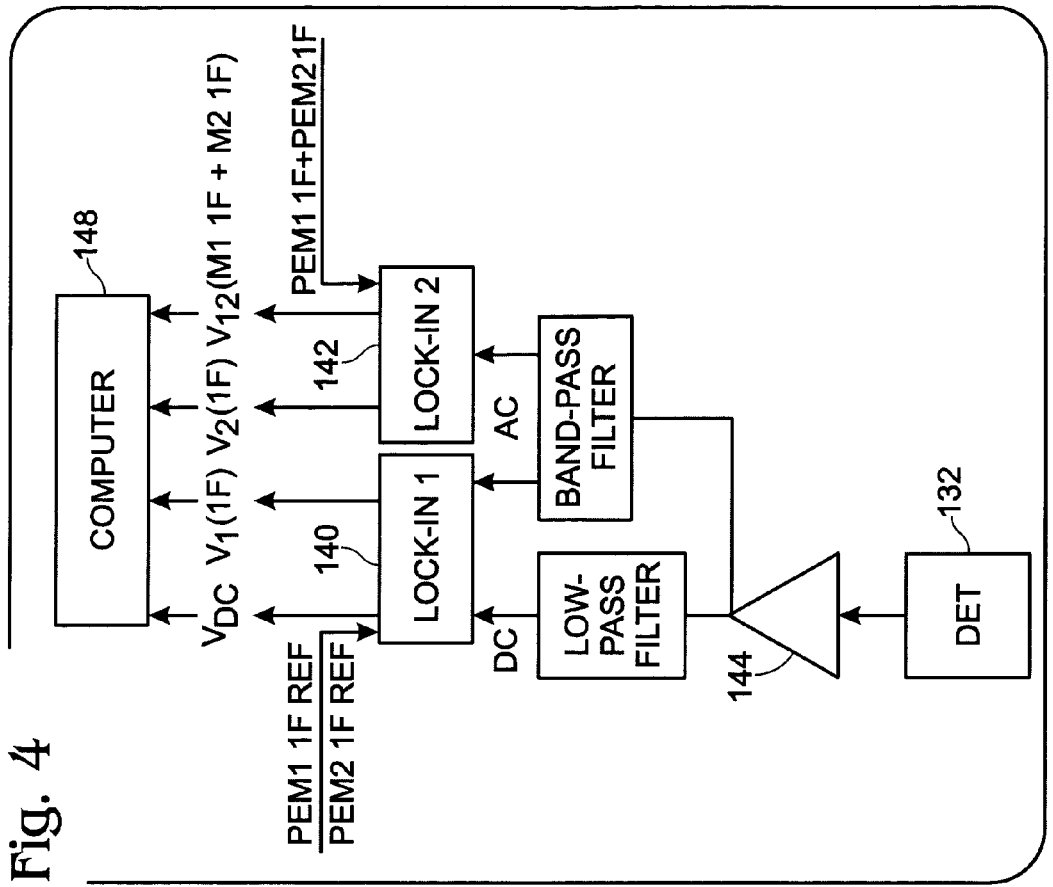
FIG. 4 is a block diagram of the processing components of the system depicted in FIG. 3.
Figure 3:
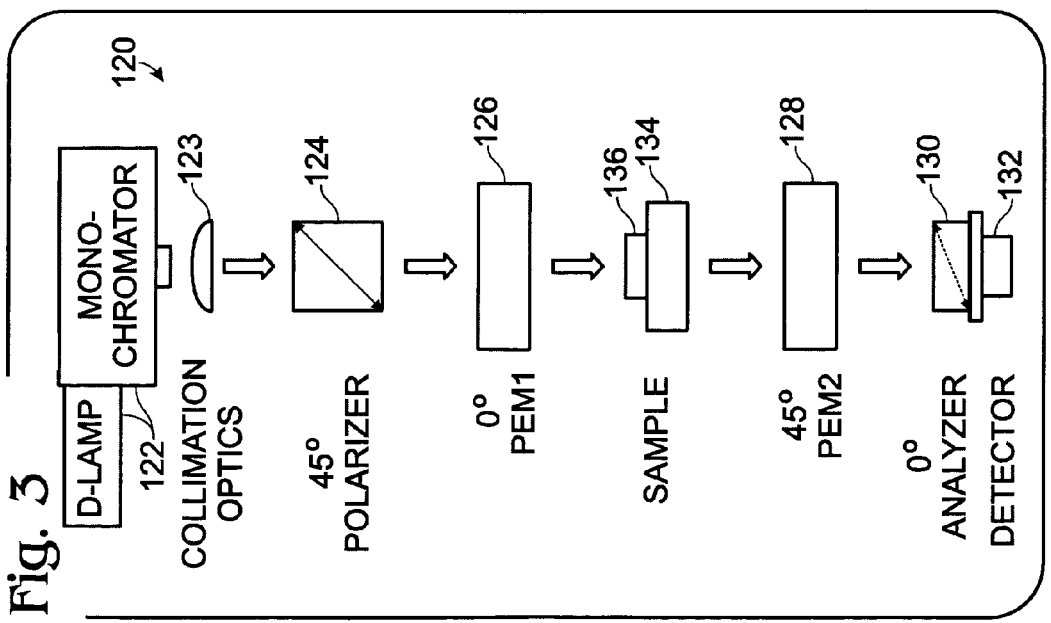
FIG. 3 is a diagram of another preferred embodiment of the present invention showing a preferred arrangement of the optical components of that birefringence measurement system.

The next described embodiment, illustrated in FIGS. 3 and 4, is suitable for accurate measurements of relatively higher levels of retardance. This is important because a commonly used optical element in a DUV environment is CaF$_2$, which has an intrinsic birefringence of about 12 nm/cm along one crystal axis. Thus, any such sample with a few cm's thickness will produce retardation higher than the just-mentioned 39 nm limit, thereby requiring a system that can measure such relatively high values of retardation, which system is described next.

As shown above, the prior-described embodiment uses the 1F signal from one PEM 26 (M11F) and the 1F signal from the other PEM 28 (M21F) to determine up to quarter-wave (e.g., 39 nm) retardation. By processing the electronic signal of the detector at the frequency of (M11F+M21F), the retardation range can be extended to half-wave of the light source's wavelength.

The theory of this extension has already been provided in the earlier embodiment, which shows the development of terms (1)–(4) above.

The important equations relating linear retardation to the detector signal at the frequency of (M11F+M21F) are listed below:

$$2J_1(\delta 1_0)\sin(\omega_1 t)\cdot 2J_1(\delta 2_0)\sin(\omega_2 t)\cdot \cos \quad \text{eqn. (10)}$$

$$\delta\sqrt{2}\cdot V_{12}(1F_{M1}+1F_{M2}) = \frac{KI_0}{2}\cdot 2J_1(\delta 1_0)\cdot 2J_1(\delta 2_0)\cos\delta$$

$$\delta = \arccos\left[\frac{\sqrt{2}\cdot V_{12}(1F_{M1}+1F_{M2})}{V_{DC}}\cdot \frac{1}{2J_1(\delta 1_0)\cdot 2J_1(\delta 2_0)}\right]$$

The retardation noted in equations (10) is from 0 to half wave. The fast axis angle is determined with the 1F data. Selectively combining the 1F data and the M11F+M21F data optimizes the determination of retardation from 0 to half-wave. For example, the M11F+M21F data is used with the 1F data for determining retardation around quarter-wave where the 1F data is not accurate. Also, the 1F data is used with the M11F+M21F data to calculate the retardation around 0 or half-wave retardation where the M11F+M21F data is not accurate.

With reference to FIG. 3, the optical setup 120 for this embodiment is in many respects the same as that described in connection with the embodiment of FIG. 1, including a polarizer 124 oriented at 45° and a PEM 126 at 0°. The system also includes a second PEM 128 that is set to a different modulation frequency (than the first PEM) and is oriented at 45 degrees, an analyzer 130 that is oriented at 0° and a detector 132. A sample holder 134 is mounted on a computer-controlled X-Y stage to allow the scan of a sample 36. Some differences in the structure and operation of these components, as compared with those of the earlier described embodiment, are described more fully below.

FIG. 4 shows the electronic signal processing block diagram of the present embodiment.

Unlike the prior embodiment, the embodiment of FIG. 3 incorporates a light source 122 that is capable of generating beams of different wavelengths in the DUV region. These beams are collimated 123, and separately directed through the sample 136 and processed as described more below.

Before describing the preferred and alternative mechanisms for providing the light source 122, the rationale underlying the need for a dual or multiple wavelength light source is discussed.

Figure 5:
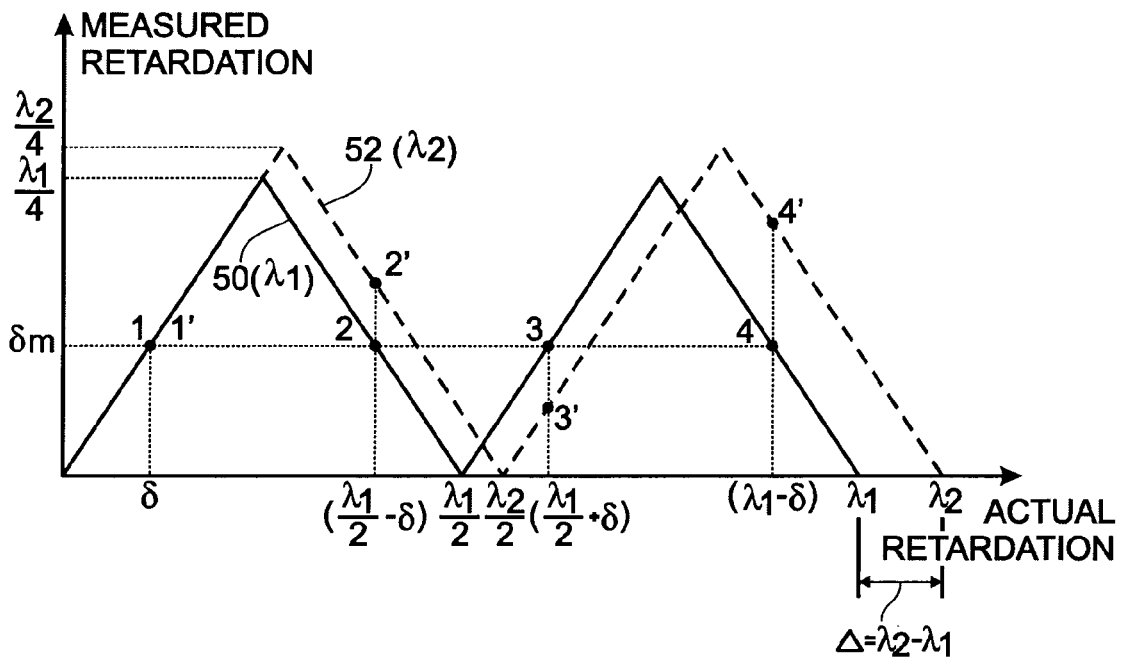
FIG. 5 is a graph depicting retardation curves for a sample measured at two different wavelengths in accord with on aspect of the present invention.

With reference to FIG. 5, a system configured, as the system illustrated in FIG. 1, to operate at a single wavelength only gives correct and unambiguous retardation measurements at low levels; namely less than one-quarter wavelength. (Occasionally the wavelength symbol lambda ($\lambda$) is hereafter used in lieu of the term wavelength.) It will be appreciated, however that without knowing in advance that the retardance value (magnitude) will be within the zero to quarter-wave range, an ambiguity will be present when the actual retardance value is calculated.

In particular, the graph of FIG. 5 shows on its ordinate the measured retardance values (determined from the analysis presented earlier). The abscissa shows actual retardance levels. Considering a single wavelength system, the intensity-related signals provided to the computer 48 (FIG. 2) and based upon a single-wavelength light source will correspond to the single wavelength trace 50 on the graph of FIG. 5 (ignoring for the moment the dashed-line second wavelength trace 52 described later).

Considering this "M" shaped, single wavelength line 50 of FIG. 5, one can see that for a given measured (by the system) retardance value $\delta_M$, there is associated with that wavelength four possible actual values of retardance $\delta$. This ambiguity appears on the abscissa at $\delta$, ($\lambda/2-\delta$), ($\lambda/2+\delta$), and ($\lambda-\delta$), within the range 0 to $\lambda$ (633 nm for this example). For example, when the instrument gives a reading of 40 nm for a measured sample, the actual retardation of the sample could be 40 nm, 277 nm, 357 nm, or 593 nm. The actual retardation of the sample could also be the above values plus any multiple order of full waves, which cannot be resolved with a single-wavelength instrument.

In accord with the embodiment of FIG. 3, two wavelengths ($\lambda_1$ and $\lambda_2$) are used for the retardation measurement, and the possible measurements that are based on these wavelengths appear in the graph of FIG. 5 as solid line 50 and dashed line 52.

In a preferred embodiment (FIGS. 3 and 4) the light source 122 comprises a deuterium lamp combined with a monochromator. The lamp irradiates a wide range of wavelengths. The monochromator selects the wavelength that is desired for the particular birefringence measurement application (such as 157 nm +/−10 nm). It is contemplated that other lamps such as mercury lamps and xenon lamps can be used for birefringence measurements in different spectral regions.

As shown in FIG. 5, the same sample has two distinct retardation curves 50, 52 when measured at the two different wavelengths (solid line for $\lambda_1$; dashed line for $\lambda_2$) provided by the light source 122 of this (FIG. 3) embodiment. The four points that reflect the ambiguity at $\delta$, ($\lambda_1/2-\delta$), ($\lambda_1/2+\delta$), and ($\lambda_1-\delta$), which are labeled as 1, 2, 3, and 4 respectively, when measured with only wavelength $\lambda_1$, have separate retardation values (labeled as 1', 2,' 3,' and 4') when measured at $\lambda_2$.

To determine the correct actual retardance of the sample in this situation, the computer 148 of the present invention is programmed to carry out the following algorithm:

1. Measure the sample at $\lambda_1$, which gives ($\delta_M$, $\rho_M$);
2. Measure the same sample at $\lambda_2$, which gives ($\delta'_M$, $\rho'_M$);
3. Using the measurement results from the two wavelengths, the sample's actual retardation can be determined:
    3.1. If $\delta_M = \delta'_M$, the sample's actual retardation is $\delta = \delta_M = \delta'_M$ and $\rho = \rho_M = \rho'_M$;
    3.2. If $\delta'_M = \delta_M + \Delta/2$ ($\Delta = \lambda 2 - \lambda 1$ and $\lambda 2 > \lambda 1$), the sample's actual retardation is $\delta = \lambda 1/2 - \delta_M$ and $\rho = \rho_M$;
    3.3. If $\delta'_M = \delta_M - \Delta/2$, the sample's actual retardation is $\delta = \lambda 1/2 + \delta_M$ and $\rho = \rho_M + 90$ degrees;
    3.4. If $\delta'_M = \delta_M + \Delta$, the sample's actual retardation is $\delta = \lambda 1 - \delta_M$ and $\rho = \rho_M + 90$ degrees.

As shown in FIG. 5, around the peaks, valleys and intersections of the two curves 50, 52 the conditions are different. When the wavelengths $\lambda_1$ and $\lambda_2$ are selected to be sufficiently different, for example, $\lambda_2$ being about 20% of the other, lower wavelength $\lambda_1$, measurement results at both wavelengths can be used to determine unambiguously what the actual retardation is within 1 full wavelength of the retardation at the longer wavelength.

One such case is when the actual retardation is close to $\lambda_1/4$ or $3\lambda_1/4$. For this case, retardation measured with $\lambda_1$ is not accurate due to the use of the arcsine function in calculating the retardation. However, the measurement result with $\lambda_2$ is accurate since the wavelengths are set far enough apart. The $\lambda_2$ results can be used to determine the actual retardation. The significant difference of the $\lambda_2$ results in the vicinity of $\lambda_1/4$ and $3\lambda_1/4$ can be used to distinguish which is the actual retardation. A preferred procedure for use in this case is as follows:

1. Measure the sample at $\lambda 1$, which gives ($\delta_M$, $\rho_M$) where $\delta_M$ is close to $\lambda 1/4$ (say within 5%);
2. Measure the same sample at $\lambda 2$, which gives ($\delta'_M$, $\rho'_M$);
3. if $\delta'_M$ is close to $\lambda 1/4$ (say within 5%), the sample's actual retardation is close to $\lambda 1/4$—($\delta = \delta'_M$, $\rho = \rho'_M$);
4. if $\delta'_M$ is close to $\lambda 1/4 - \Delta/2$ (say within 5%), the sample's actual retardation is close to $3\lambda 1/4$. In this case, the sample's actual retardation is—($\delta = \delta'_M + \Delta/2 + \lambda 1/2$; $\rho = \rho_M + 90$).

Similarly, when the actual retardation is close to $\lambda_2/4$, $3\lambda_2/4$, $\lambda_1/2$, $\lambda_2/2$, $\lambda_1$, $\lambda_2$, or the intersections of the two curves 50, 52, the sample's actual retardation can be determined using the combination of measurement results from $\lambda_1$ and $\lambda_2$.

In one embodiment, such as where the sample is under consideration is comprised of $CaF_2$, $\lambda_1$ is selected to be 157 nm and $\lambda_2$ maybe, for example, 165 nm.

It is noteworthy here that other light sources are contemplated in this embodiment. For example, the light source can be two or more separate lasers at different wavelengths. A switching device, such as a flip mirror, can allow the individual beams to pass to the sample, one at a time. Alternatively, the source can be a tunable laser that offers multiple wavelengths. Wavelength selection can then be determined by the computer-controlled system.

Another choice of light source is a laser that emits multiple wavelengths simultaneously. To select the wavelengths for birefringence measurement, one can employ an optical filter wheel to selectively pass the proper wavelengths. A filter wheel contains multiple optical filters mounted to the wheel. Rotation of the wheel allows a certain optical filter to be inserted into the path of the light beam.

It is also possible to use a broadband light source combined with a filter wheel or wheels to select the desired wavelengths. Different types of optical filters, including high-pass, low-pass, and band pass filters, can be used in the filter wheel. A combination of filter wheels can be applied when necessary.

The computer 148 is used to control and coordinate selecting wavelengths from the light source, as well as driving the PEMs at an optimal level for measuring birefringence and collecting data at an optimized sequence and calculating the final results.

It is pointed out that although FIG. 4 shows two lock-in amplifiers 140, 142, that number can be different. For example, the use of one lock-in amplifier to detect sequentially the signals at different frequencies is also contemplated. Three lock-in amplifiers to detect M11F, M21F, and M11F+M21F signals simultaneously are also contemplated. Once can also use a combination of sequential and simultaneous measurements.

When lock-in amplifiers are used in the system (FIG. 4), the method described above only requires the use of 1F data from both PEMs. When the (M11F +M21F) data is collected in addition to the 1F data of the two PEMs, the range of measurable birefringence is extended to half wave at each wavelength used. In this case, the retardation curve at each wavelength becomes one triangle with its maximum at half-wave of the corresponding wavelength, as compared to two triangles for each wavelength with its maximum at quarter-wave of the corresponding wavelength as shown in FIG. 5. Collecting the extra data simplifies the analysis.

When the birefringence dispersion at the chosen wavelengths is not negligible, this effect must be taken into account. For a specific sample, the birefringence at two chosen wavelengths is related by a constant determined by the material's dispersion. When the dispersion is unknown, it can be measured with a calibrated birefringence measurement system. Correction of birefringence dispersion is necessary for measurements around 157 nm.

In instances where the sample 136 has retardation higher than 1 full wave ($\lambda$1), the relationship described above is modified for determining the actual retardation. In this case, it is preferable that $\lambda$1 and $\lambda$2 are close so that when the sample is measured at the two wavelengths, the retardation measured will be at the same order, i.e. $m\lambda_1+\delta_1$ and $m\lambda_2+\delta_2$. It is easy to select wavelengths when a white light source combined with a monochromator is used.

It is possible that there is still ambiguity for some discrete data points when very large retardation values are involved, such as retardation satisfying $(m+1)\lambda_1 = m\lambda_2$. In such cases, a third wavelength can be used to tell them apart.

Figure 6:
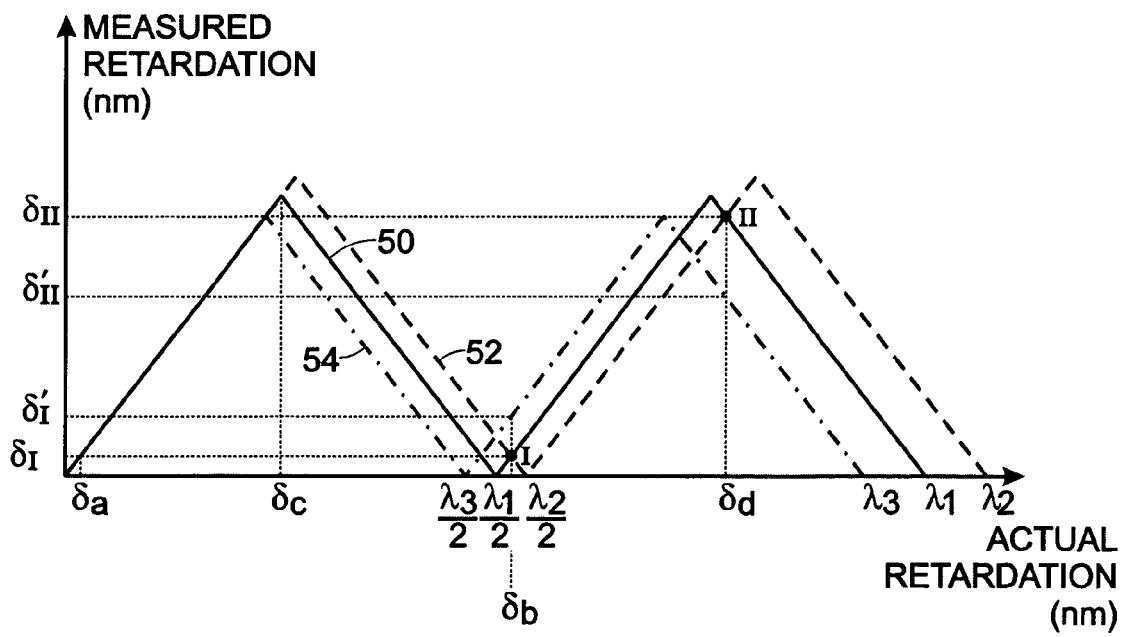
FIG. 6 is a graph depicting retardation curves for a sample measured at three different wavelengths in accord with another aspect of the present invention.

More particularly, when only two wavelengths are used, the two curves representing the two wavelengths intersect at two positions (FIG. 5). There are ambiguities in determining the actual retardation at those two positions. In FIG. 6, these two intersections are labeled I and II. The actual retardation for those two positions are $\delta b$ and $\delta d$, respectively. The measured retardation for the two positions are $\delta I$ and $\delta II$. There are ambiguities between $\delta a$ and $\delta b$ as well as between $\delta c$ and $\delta d$. One solution to resolve the ambiguities is to use a third wavelength, as shown by the retardance curve 54 in FIG. 6, which curve 54 is associates with the third wavelength. Using the third wavelength gives very different results, $\delta I'$ and $\delta II'$, for the positions I and II, respectively.

It is important to point out that there are only a very limited number of data points where there is any such ambiguity. For example, two wavelengths are sufficient to measure all retardation below $\lambda/2$ without any ambiguity. A third wavelength is only required when the measured retardation are at $\delta I$ and $\delta II$ (within the error of the measurement in reality) to determine the actual retardation.

Upon further consideration of FIG. 6, it will be appreciated that, as the actual retardation increases, it is possible that all three curves intersect at the same position. In this case, $\lambda 1$, $\lambda 2$, and $\lambda 3$ will all give the same measurement result. A fourth wavelength could then be used to resolve the ambiguities and determine the actual retardation. Similarly, in rare cases, more than four wavelengths may be required for resolving ambiguities for very high levels of retardation.

The foregoing analyses provide various processes for measuring birefringence. Some processes or modes are more efficient than others, depending generally upon the magnitude of the retardation to be measured. What follows is a useful method for selecting the appropriate process for given ranges of estimated birefringence.

1. Preferred Process For Measuring Small Linear Birefringence (<0.35 Radian or 35 nm Using 632.8 He—Ne Laser)

When the samples studied have small linear birefringence, the DC signal can be derived from term (1) to be:

$$V_{DC} = \frac{KI_0}{2}\left\{1 + J_0(\delta 1_0)\cdot J_0(\delta 2_0)\cdot \sin(4\rho)\sin^2\left(\frac{\delta}{2}\right)\right\} \quad \text{eqn. (5)}$$

where any term that varies as a function of the PEMs' modulation frequencies is omitted because they have no net contribution to the DC signal. A low-pass electronic filter is used to eliminate such oscillations. Within small angle approximation (sin X=X and sin$^2$X=0 when X is small), $V_{DC}$ is independent of the sample's retardation and the PEMs' peak retardation setting, and thus represents the average light intensity reaching the detector.

$$V_{DC} = \frac{KI_0}{2}. \quad \text{eqn. (6)}$$

Therefore, the PEMs' peak retardation setting can be set at 1.43 radians to maximize the values of $J_0(\delta 1_0)2J_1((\delta 2_0)$ and $J_0(\delta 2_0)2J_1((\delta 1_0)$, thus to optimize the 1F AC signal recovery using lock-in amplifiers. At the PEMs' peak retardation setting of 1.43 radians, the effect of the magnitude of a retardance in the worst case (sin(4$\rho$)=1) on $V_{DC}$ is such that the maximum error for the DC signal will not exceed 1% and 2% for retardation below 35 nm and 50 nm, respectively.

When the linear retardance in a sample is small, an instrument based on detecting both the DC signal and 1F AC signals at PEMs' peak retardation setting of 1.43 radians, offers high sensitivity and fast measurements. The sensitivity is better than 0.005 nm using a 632.8 nm He—Ne laser as the light source. The speed of data collection is effectively determined by the time constant setting on the lock-in amplifiers.

2. Preferred Process for Measuring Relatively Higher Linear Retardation (0.35 Radians to $\pi/2$)

When a 632.8 nm He—Ne laser is used as the light source, the effect on the DC signal from a sample with retardation above 35 nm should not be neglected. In this case, the most straightforward method is to set both $J_0(\delta 1_0)$ and $J_0(\delta 2_0)$ equal to "0". At the PEMs' retardation amplitude $\delta 1_0 = \delta 2_0 = 2.405$ radians (0.3828 waves), the DC signal, independent of $\rho$ or $\delta$, truly indicates the average light intensity reaching the detector.

However, it is clear from equation (4):

$$\sqrt{2} \cdot V_{1,1F} = \frac{KI_0}{2} J_0(\delta 1_0) \cdot 2J_1(\delta 2_0) \cos(2\rho) \sin\delta \qquad \text{eqn. (4)}$$

$$\sqrt{2} \cdot V_{2,1F} = \frac{KI_0}{2} J_0(\delta 2_0) \cdot 2J_1(\delta 1_{01}) \sin(2\rho) \sin\delta$$

that the 1F AC signals from both PEMs cannot be collected at PEM settings of $J_0(\delta 1_0) = J_0(\delta 2_0) = 0$ at which the DC signal is recorded. For measuring higher levels of linear retardation (35 nm or 0.35 rad. to 158 nm or $\pi/2$), the method described here requires recording AC and DC signals at different PEM settings, thus has a slower measurement speed (about 2 seconds per data point).

When speed is critical, an alternative method can be used. If the DC signal is collected at $\delta 1_0 = \delta 2_0 = 1.43$ radians where the AC signals are recorded, the measured retardance of a sample, using the ratio of AC to DC, will depend on the sample's angular orientation. However, the DC term is well defined in equation (4). It is, therefore, possible to reduce the angular dependence of retardance by iteration of calculation for both retardation magnitude and angle.

3. Preferred Process For Measuring Linear Retardation up to $\pi$ or 316.4 nm Using 632.8 He—Ne Laser When a 632.8 nm He—Ne laser is used as the light source, a combination of the above mentioned processes and the use of term (2) can be employed to determine linear retardance up to half wave (316.4 nm) or $\pi$. This process will involve:

1. measuring retardation (both magnitude and angle of fast axis) up to 0.35 rad. using process 1
2. measuring retardation (both magnitude and angle of fast axis) from 0.35 to $\pi/4$ using process 2
3. for retardation from $\pi/4$ to $\pi/4$, measuring retardation magnitude using term (2) and measuring retardation angle using process 2
4. measuring retardation from $3\pi/4$ to n using process 2 with modified algorithm ($\delta_{actual} = \pi - \delta_{1F}$)

The combination of different processes will give the most accurate measurement results for linear birefringence measurement from 0 to $\pi$.

In any of the preferred mode, the light source can be a variety of choices as proposed earlier.

Figure 7:
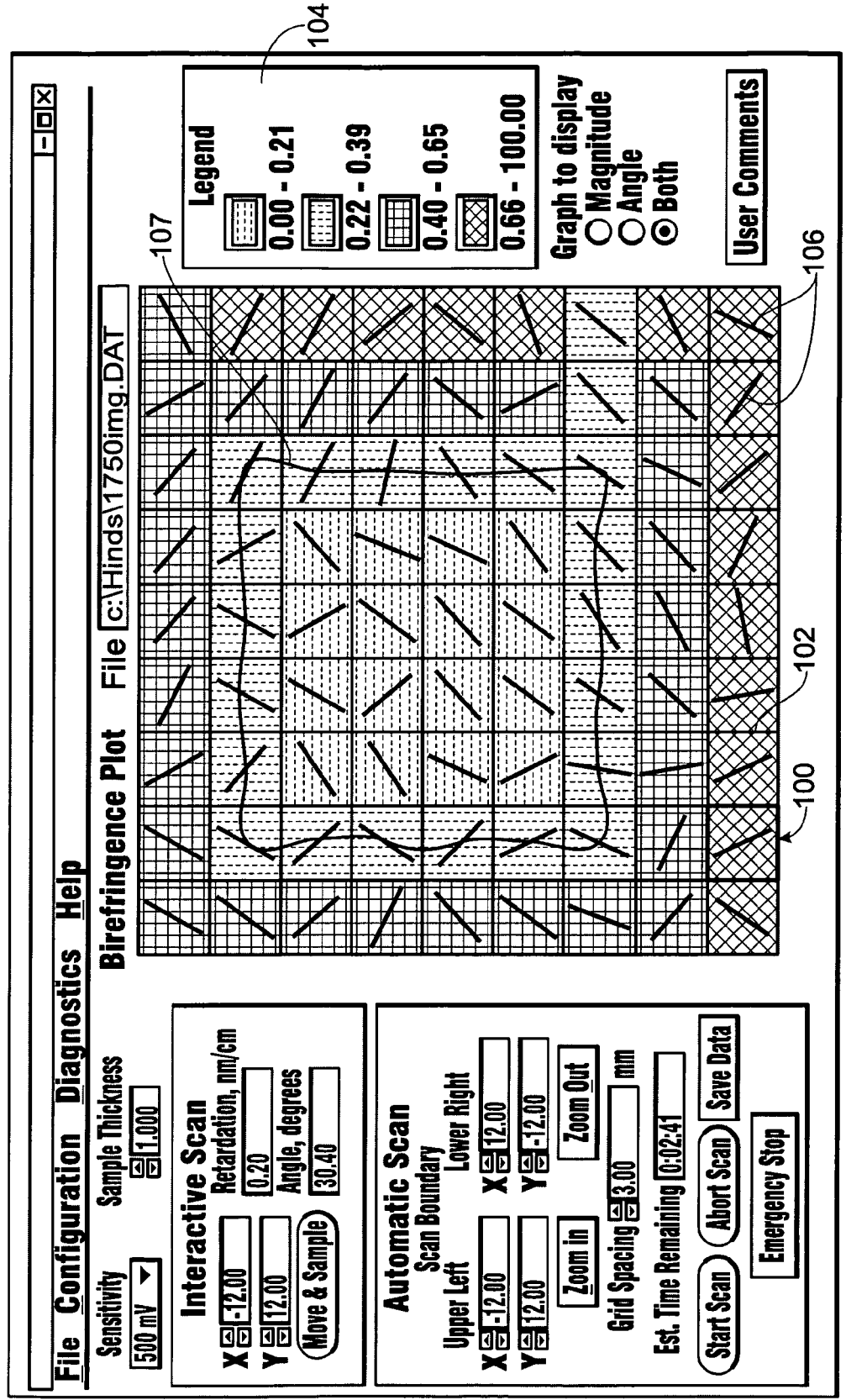
FIG. 7 is a drawing depicting a graphical display provided by the system of the present invention.

The measured retardance values can be handled in a number of ways. In a preferred embodiment the data collected from the multiple scans of a sample are stored in a data file and displayed as a plot on a computer display. One such plot 100 is shown in FIG. 7. Each cell 102 in a grid of cells in the plot indicates a discrete location on the sample. The magnitude of the retardance is depicted by color coding. Here different shadings in the cells represent different colors.

In FIG. 7, only a few different colors and cells are displayed for clarity. It will be appreciated, however, that a multitude of cells can be displayed. The legend 104 on the display correlates the colors (the color shading is omitted from the legend) to a selectable range of retardance values within which the particular measurement associated with a cell 102 falls. A line 106 located in each cell 102 extends across the center of each cell and presents an unambiguous visual indication of the full physical range ($-90°$ to $+90°$) of the orientation of the fast axis of the sample at each sampled location. Thus, the orientation of the fast axis and the retardance magnitude measurements are simultaneously, graphically displayed for each location. With such a complete, graphical display, an inexperienced operator user is less likely to make errors in analyzing the data that are presented.

In a preferred embodiment, the just described retardance measurements are displayed for each cell as soon as that cell's information is computed. As a result of this instantaneous display approach, the operator observes the retardance value of each cell, without the need to wait until the retardance values of all of the cells in the sample have been calculated. This is advantageous for maximizing throughput in instances where, for example, an operator is charged with rejecting a sample if the birefringence value of any part of the sample exceeds an established threshold.

Also illustrated in FIG. 7 is a contour line placed there as an example of a contour line that follows a common measured range of retardation magnitude. For simplicity, only a single one of several contour lines is shown for the low-resolution plot of FIG. 7.

It will be appreciated that any of a number of variations for displaying the measured data will suffice. It will also be apparent from FIG. 7 that the means for setting parameters of how the sample is scanned (scan boundaries, grid spacing sample thickness, etc.) and the resulting data are conveniently, interactively displayed.

Another approach to graphically displaying the retardance magnitude and orientation information provided by the present system is to depict the retardance magnitude for a plurality of locations in a sample via corresponding areas on a three-dimensional contour map. The associated orientations are simultaneously shown as lines or colors in corresponding cells in a planar projection of the three dimensional map.

While the present invention has been described in terms of preferred embodiments, it will be appreciated by one of ordinary skill in the art that modifications may be made without departing from the teachings and spirit of the foregoing. For example, it is also contemplated that other source wavelengths may be used with the embodiments described above. Representative ones of such wavelengths are 193 nm and 248 nm.

What is claimed is:

1. A method of determining a birefringence property of a sample, comprising the steps of:
    separately directing through the sample a first beam of polarization-modulated light having a first wavelength and a second beam of polarization-modulated light having a second wavelength, the first and second wavelengths being different;
    modulating the polarization of the first and second beams after those beams pass through the sample;
    analyzing the first and second beams;
    detecting the intensity of the first and second beams; and
    calculating an actual birefringence property of the sample based on the detected intensities.

2. The method of claim 1 wherein calculating includes:
identifying two or more measured birefringence properties; and
determining the actual birefringence property from among the measured birefringence properties.

3. The method of claim 2 wherein the determining step includes selecting the actual birefringence property from among the identified measured birefringence properties depending upon differences between the measured birefringence properties as compared to differences between the first and second wavelengths.

4. The method of claim 2 wherein the determining step includes selecting the actual birefringence property to be one of the measured birefringence properties in instances where the one treasured birefringence properties is equal to another measured birefringence property.

5. The method of claim 1 further comprising the step of determining the actual birefringence property to include magnitude.

6. The method of claim 1 further comprising the step of determining the actual birefringence property to include angular orientation.

7. The method of claim 1 further comprising the step of determining the actual birefringence property to include both magnitude and angular orientation.

8. The method of claim 1 including the step of providing the first and second wavelengths to be about 157 nanometers.

9. The method of claim 8 including the step of providing the sample as a calcium fluoride optical element.

10. The method of claim 1 including the step of providing a sample that is selected to be of a thickness such that the actual birefringence property will include a magnitude that is greater than one quarter of either the first or second wavelengths.

11. The method of claim 10 wherein the sample is selected to be of a thickness such that the actual birefringence property will include a magnitude that is as large as either the first or second wavelengths.

12. The method of claim 2 wherein the determining stop includes selecting die actual birefringence property from among the identified measured birefringence properties depending upon how near the magnitude of one of the identified measured birefringence properties is to one-quarter increments of the first wavelength.

13. The method of claim 12 including the step of selecting the second wavelength to be about 20% of the first wavelength.

14. The method of claim 1 including the steps of:
periodically moving the sample so that the beams are directed through a plurality of locations on the sample; and
calculating an actual retardance property of the sample at each location.

15. The method of 1 including the step of simultaneously graphically displaying the retardance magnitude and angular orientation of substantially all of the locations.

16. A method of measuring birefringence properties of a sample, comprising the steps of:
separately directing through die sample at least three light beams comprising a first beam of polarization-modulated light having a first wavelength, a second beam of polarization-modulated light having a second wavelength, and a third beam of polarization-modulated light having a third wavelength, the first, second, and third wavelengths being different from one another;
modulating the polarization of the first, second, and third beams after those beams pass through the sample;
analyzing the first, second, and third beams;
detecting the intensity of the first, second, and third beams; and
calculating an actual birefringence property of the sample based on the detected intensities.

17. The method of claim 1 wherein calculating includes:
identifying three or more measured birefringence properties; and
determining the actual birefringence property from among the measured birefringence properties.

18. The method of claim 17 wherein the determining step includes selecting the actual birefringence property to be one of the measured birefringence properties in instances where the one measured birefringence property is equal to another measured birefringence property.

19. A system for measuring birefringence properties in a sample, comprising:
a source of two or more beams of light having wavelengths that are different from one another;
means for modulating the polarization of the light beams, including two photoelastic modulators arranged with the sample between the photoelastic modulators;
means for separately directing the beams through the sample;
means for analyzing the beams after the beams pass through the sample; and
detection means for detecting the intensity of the beams and using the detected intensities to provide information suitable for calculating a birefringence property of the sample based on the detected intensifies.

20. The system of claim 19 wherein the means for separately directing includes a deuterium lamp and a monochromator.

21. The system of claim 19 wherein the sample comprises calcium fluoride having a thickness of up to about 270 millimeters.

22. The system of claim 19 wherein the wavelengths of the source light are about 157 nanometers.

* * * * *